US008889161B2

(12) United States Patent
Latta et al.

(10) Patent No.: US 8,889,161 B2
(45) Date of Patent: Nov. 18, 2014

(54) MICROENCAPSULATED COMPOSITIONS AND METHODS FOR TISSUE MINERALIZATION

(75) Inventors: Mark A. Latta, Omaha, NE (US);
Stephen M. Gross, Omaha, NE (US);
William A. Mchale, Collegeville, PA (US)

(73) Assignee: Premier Dental Products Company, Plymouth Meeting, PA (US)

( * ) Notice: Subject to any disclaimer, the term of this patent is extended or adjusted under 35 U.S.C. 154(b) by 354 days.

(21) Appl. No.: 12/768,696

(22) Filed: Apr. 27, 2010

(65) Prior Publication Data
US 2010/0272764 A1 Oct. 28, 2010

Related U.S. Application Data

(60) Provisional application No. 61/172,939, filed on Apr. 27, 2009.

(51) Int. Cl.
| | | |
|---|---|---|
| A61K 8/02 | (2006.01) |
| A61K 9/48 | (2006.01) |
| A61K 9/66 | (2006.01) |
| A61K 8/00 | (2006.01) |
| A61K 8/18 | (2006.01) |
| A61K 8/21 | (2006.01) |
| A61K 8/30 | (2006.01) |
| A61K 8/46 | (2006.01) |
| A61K 9/14 | (2006.01) |
| A61K 9/16 | (2006.01) |
| A61K 9/50 | (2006.01) |
| A61Q 11/00 | (2006.01) |
| A61K 8/11 | (2006.01) |
| A61K 8/19 | (2006.01) |
| A61K 8/24 | (2006.01) |
| A61K 9/00 | (2006.01) |
| A61K 33/06 | (2006.01) |
| A61K 33/16 | (2006.01) |
| A61K 33/44 | (2006.01) |
| A61K 47/02 | (2006.01) |

(52) U.S. Cl.
CPC ... *A61K 8/11* (2013.01); *A61K 8/19* (2013.01); *A61K 8/21* (2013.01); *A61K 8/24* (2013.01); *A61K 9/0056* (2013.01); *A61K 9/5031* (2013.01); *A61K 9/5089* (2013.01); *A61K 33/06* (2013.01); *A61K 33/16* (2013.01); *A61K 33/44* (2013.01); *A61K 47/02* (2013.01); *A61Q 11/00* (2013.01); *A61K 2800/412* (2013.01)
USPC .......... 424/401; 424/451; 424/455; 424/489; 424/497; 424/49; 424/52; 424/57

(58) Field of Classification Search
CPC .......... A61K 33/06; A61K 8/24; A61K 8/19; A61K 9/5005; A61K 9/5089; A61K 9/5031
USPC ........ 424/401, 451, 455, 489, 497, 49, 52, 57
See application file for complete search history.

(56) References Cited

U.S. PATENT DOCUMENTS

| | | | |
|---|---|---|---|
| 3,442,842 A | 5/1969 | Bonin | |
| 4,652,441 A | 3/1987 | Okada et al. | |
| 4,711,782 A | 12/1987 | Okada | |
| 5,665,382 A | 9/1997 | Grinstaff et al. | |
| 5,910,492 A * | 6/1999 | Hoshino et al. | 514/114 |
| 5,911,923 A | 6/1999 | Work et al. | |
| 5,925,595 A | 7/1999 | Seitz et al. | |
| 6,534,091 B1 | 3/2003 | Graces et al. | |
| 2002/0090398 A1 | 7/2002 | Dunn et al. | |
| 2004/0136961 A1 | 7/2004 | Prokop et al. | |
| 2008/0152598 A1 | 6/2008 | Basic | |
| 2008/0175918 A1 | 7/2008 | Laulicht | |
| 2011/0104052 A1* | 5/2011 | Barnett et al. | 424/1.21 |

FOREIGN PATENT DOCUMENTS

| | | |
|---|---|---|
| CN | 1187122 | 7/1998 |
| JP | 2004-025099 | 1/2004 |
| WO | WO 96/39134 | 12/1996 |

OTHER PUBLICATIONS

Lowenstam et al., Science 188: 363 (1975).*
Tung, Ming S., CE2, Amorphous Calciuum Phosphates for Tooth Mineralization, Sep. 2004, vol. 25, No. 9, American Dental Association Foundation.
Charig, Andrew, CE 3, Enamel Mineralization by Calcium-containing Bicarbonete Toothpastes: Assessment by Various Techniques, Compendium, Sep. 2004, vol. 25, No. 9.
Litkowski, Leonard J., CE4, Intraoral Evaluation of Mineralization of Cosmetic Defects by a Toothpaste Containing Calcium, Fluoride, and Sodium Bicarbonate, Compendium, Sep. 2004, vol. 25, No. 9.
Schemehorn, B.R., Remineralization by Fluoride Enhanced with Calcium and Phosphate Ingredients, Indiana University School of Dentistry, The British Library, Enamelon, Inc., Cranbury, NJ.
Xu, HHK, Strong Nanocomposites with Ca PO4, and F Release for Caries Inhibition, Critical Reviews in Oral Biology & Medicine, Jan. 2009.
Roveri, Norberto, Surface Enamel Remineralization: Biomimelic Apatite Nanocrystals and Fluoride Ions Different Effects, vol. 2009, Article ID 746383, Journal of Nanomaterials.
Thies, Curt, A Survey of Microencapsulation Processes, Washington University, St. Louis, MO.

(Continued)

*Primary Examiner* — Abigail Fisher
(74) *Attorney, Agent, or Firm* — Cozen O'Connor

(57) ABSTRACT

The present invention is directed to compositions, products and methods useful for bone and tooth mineralization. The compositions comprise polymer microcapsules containing aqueous salt solutions. The shells of the microcapsules can be semi-permeable or impermeable. Solutions of calcium, fluoride and phosphate salts are particularly useful in the compositions of the invention. The microcapsules are preferably prepared by surfactant free inverse emulsion interfacial polymerization. Bone products include cements, scaffolds and bioactive glass. Dental products include pastes, gels, rinses and many other dental materials.

35 Claims, 1 Drawing Sheet

(56) References Cited

OTHER PUBLICATIONS

Lei, Y., In Vitro Degradation of novel Biocative Polycarprolactone—20% Tricalcium Phosphate Composite Scaffolds for Bone Engineering, Materials and Science and Engineering, vol. 27, Issue 2, Mar. 2007.

Jacob M. ten Cate "Current concepts on the theories of the Mechanism of Action of Fluoride" Academic Centre for Dentistry Amsterdam (ACTA), Department of Cariology Endodontology Pedodontology, Amsterdam the Netherlands, pp. 325-329, (1999).

Wu et al., "Preparation of Sodium Fluoride-Loaded Gelatin Microspheres, Characterization and Cariostatic Studies", Dec. 2004, vol. 21, No. 8, p. 889-903.

Laguecir et al., "Influence of the Monomers Type on the Morphology of Polyamide Microcapsules", 2004, p. 111-117.

Kawakatsu et al, "Production of W/O/W Emulsions and S/O/W Pectin Microcapsules by Microchannel Emulsification", 2000, p. 257-264.

Collected Articles of Chemical Engineering, 2000, vol. 26, No. 1, p. 122-125.

* cited by examiner

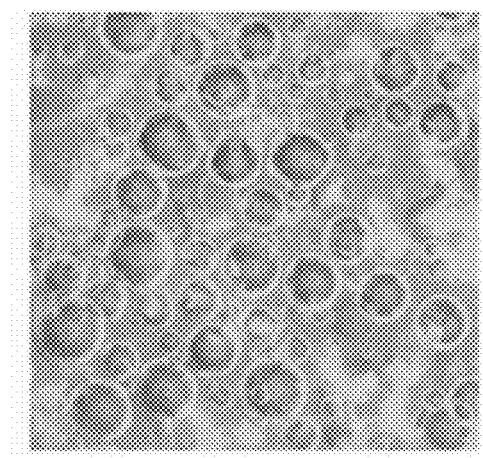

MICROENCAPSULATED COMPOSITIONS AND METHODS FOR TISSUE MINERALIZATION

CROSS-REFERENCE TO RELATED APPLICATIONS

The present application claims the benefit of U.S. Provisional Application No. 61/172,939, filed on Apr. 27, 2009 which is incorporated herein by reference.

STATEMENT REGARDING FEDERALLY SPONSORED RESEARCH OR DEVELOPMENT

The present invention was not developed with the use of any Federal Funds, but was developed independently by the inventors.

BACKGROUND OF THE INVENTION

The present invention is directed to compositions, compounds and methods for the mineralization of various physiological tissues, primarily of bone and teeth. Mineralized connective tissue or tissues include teeth, bone, and various connective tissues such as collagen, cartilage, tendons, ligaments and other dense connective tissue and reticular fibers (that contains type III collagen) of a mammal, including a human being. For purposes of definition in this specification, "mineralized tissue" shall mean bone and teeth specifically. Each of the terms "mineralization", "tissue mineralization", used interchangeably herein, means a process in which crystals of calcium phosphate are produced by bone-forming cells or tooth-forming cells and laid down in precise amounts within the fibrous matrix or scaffolding of the mineralized tissue as defined hereinabove.

Calcium phosphates are a class of minerals containing, but not limited to, calcium ions together with orthophosphates, metaphosphates and/or pyrophosphates that may or may not contain hydrogen or hydroxide ions.

For purposes of definition in this specification, "remineralization" is the process of restoring minerals, in the form of mineral ions, to the hydroxyapatite latticework structure of a tooth. As used herein, the term "remineralization" includes mineralization, calcification, re-calcification and fluoridation as well as other processes by which various particular ions are mineralized to the tooth. The term "teeth" or "tooth" as used herein includes the dentin, enamel, pulp and cementum of a tooth within the oral cavity of an animal, including a human being.

In certain embodiments, the present invention provides methods for whitening the surface of a tooth material by using the compositions of the invention. For purposes of definition in this specification, as referred to herein, a "tooth material" refers to natural teeth, dentures, dental plates, fillings, caps, crowns, bridges, dental implants, and the like, and any other hard surfaced dental prosthesis either permanently or temporarily fixed to a tooth within the oral cavity of an animal, including a human being. As used herein, the terms "whitening" and "tooth whitening" used interchangeably, refer to a change in the visual appearance of a tooth as defined herein, preferably such that the tooth has a brighter shade or luster.

Conditions of the Bone

No currently practiced therapeutic strategy involves methods or compositions that sufficiently stimulate or enhance the growth of new bone mass. The present invention provides compositions, products and methods which serve to increase bone mineralization at localized sites or remineralization of teeth directly in the oral cavity, and thus may be utilized in conjunction with treatments of a wide variety of conditions where it is desired to increase bone or tissue mass as a result of any condition which can be improved by bioavailability of physiological salts, particularly of calcium and phosphate.

Certain changes in bone mass occur over the life span of an individual. After about the age of 40 and continuing to the last stages of life, slow bone loss occurs in both men and women. Loss of bone mineral content can be caused by a variety of conditions, and may result in significant medical problems. If the process of tissue mineralization is not properly regulated, the result can be too little of the mineral or too much—either of which can compromise bone health, hardness and strength. A number of bone growth disorders are known which cause an imbalance in the bone remodeling cycle. Chief among these are metabolic bone diseases such as osteoporosis, osteoplasia (osteomalacia), chronic renal failure and hyperparathyroidism, which result in abnormal or excessive loss of bone mass known as osteopenia. Other bone diseases, such as Paget's disease, also cause excessive loss of bone mass at localized sites.

Osteoporosis is a structural deterioration of the skeleton caused by loss of bone mass resulting from an imbalance in bone formation, bone resorption, or both. Bone resorption is the process by which osteoclasts break down bone and release the minerals, resulting in a transfer of calcium from bone fluid to the blood. Bone resorption dominates the bone formation phase, thereby reducing the weight-bearing capacity of the affected bone. In a healthy adult, the rate at which bone is formed and resorbed is tightly coordinated so as to maintain the renewal of skeletal bone. However, in osteoporotic individuals, an imbalance in these bone remodeling cycles develops which results in both loss of bone mass and in formation of micro-architectural defects in the continuity of the skeleton. These skeletal defects, created by perturbation in the remodeling sequence, accumulate and finally reach a point at which the structural integrity of the skeleton is severely compromised and bone fracture is likely. Although this imbalance occurs gradually in most individuals as they age, it is much more severe and occurs at a rapid rate in postmenopausal women. In addition, osteoporosis also may result from nutritional and endocrine imbalances, hereditary disorders and a number of malignant transformations.

Osteoporosis in humans is preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). Osteoporosis is one of the most expensive diseases for the health care system, costing billions of dollars annually in the United States. In addition to health care related costs, long-term residential care and lost working days add to the financial and social costs of this disease. Worldwide, approximately 75 million people are at risk for osteoporosis.

The frequency of osteoporosis in the human population increases with age, and among Caucasians is predominant in women, who comprise approximately 80% of the osteoporosis patient pool in the United States. In addition in women, another phase of bone loss occurs possibly due to postmenopausal estrogen deficiencies. During this phase of bone loss, women can lose an additional 10% in the cortical bone and 25% from the trabecular compartment. The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women correlate with high rates of mortality and morbidity.

Patients suffering from chronic renal (kidney) failure almost universally suffer loss of skeletal bone mass, termed renal osteodystrophy. While it is known that kidney malfunction causes a calcium and phosphate imbalance in the blood, to date replenishment of calcium and phosphate by dialysis does not significantly inhibit osteodystrophy in patients suffering from chronic renal failure. In adults, osteodystrophic symptoms often are a significant cause of morbidity. In children, renal failure often results in a failure to grow, due to the failure to maintain and/or to increase bone mass.

Osteoplasia, also known as osteomalacia ("soft bones"), is a defect in bone mineralization (e.g., incomplete mineralization), and classically is related to vitamin D deficiency (1,25-dihydroxy vitamin D3). The defect can cause compression fractures in bone, and a decrease in bone mass, as well as extended zones of hypertrophy and proliferative cartilage in place of bone tissue. The deficiency may result from a nutritional deficiency (e.g., rickets in children), malabsorption of vitamin D or calcium, and/or impaired metabolism of the vitamin.

Hyperparathyroidism (overproduction of the parathyroid hormone) is known to cause malabsorption of calcium, leading to abnormal bone loss. In children, hyperparathyroidism can inhibit growth, in adults the skeleton integrity is compromised and fracture of the ribs and vertebrae are characteristic. The parathyroid hormone imbalance typically may result from thyroid adenomas or gland hyperplasia, or may result from prolonged pharmacological use of a steroid. Secondary hyperparathyroidism also may result from renal osteodystrophy. In the early stages of the disease, osteoclasts are stimulated to resorb bone in response to the excess hormone present. As the disease progresses, the trabecular bone ultimately is resorbed and marrow is replaced with fibrosis, macrophages and areas of hemorrhage as a consequence of microfractures, a condition is referred to clinically as osteitis fibrosa.

Paget's disease (osteitis deformans) is a disorder currently thought to have a viral etiology and is characterized by excessive bone resorption at localized sites which flare and heal but which ultimately are chronic and progressive, and may lead to malignant transformation. The disease typically affects adults over the age of 25.

Although osteoporosis has been defined as an increase in the risk of fracture due to decreased bone mass, none of the presently available treatments for skeletal disorders can substantially increase the bone density of adults. A strong perception exists among physicians that drugs are needed which could increase bone density in adults, particularly in the bones of the wrist, spinal column and hip that are at risk in osteopenia and osteoporosis.

Current strategies for the prevention of osteoporosis may offer some benefit to individuals but cannot ensure resolution of the disease. These strategies include moderating physical activity, particularly in weight-bearing activities, with the onset of advanced age, including adequate calcium in the diet, and avoiding consumption of products containing alcohol or tobacco. For patients presenting with clinical osteopenia or osteoporosis, all current therapeutic drugs and strategies are directed to reducing further loss of bone mass by inhibiting the process of bone absorption, a natural component of the bone remodeling process that occurs constitutively.

For example, estrogen is now being prescribed to retard bone loss. There is, however, some controversy over whether there is any long term benefit to patients and whether there is any effect at all on patients over 75 years old. Moreover, use of estrogen is believed to increase the risk of breast and endometrial cancer. High doses of dietary calcium with or without vitamin D have also been suggested for postmenopausal women. However, ingestion of high doses of calcium can often have unpleasant gastrointestinal side effects, and serum and urinary calcium levels must be continuously monitored.

Other therapeutics which have been suggested include calcitonin, bisphosphonates, anabolic steroids and sodium fluoride. Such therapeutics however, have undesirable side effects, for example, calcitonin and steroids may cause nausea and provoke an immune reaction, bisphosphonates and sodium fluoride may inhibit repair of fractures, even though bone density increases modestly, which that may prevent their usage.

The above disorders are examples of conditions that may lead to bone fractures, fissures or splintering of the bones in the individuals who suffer from a given disorder. Current therapeutic methods are insufficient to treat the disorders leaving a need for improved treatments of bone fractures when they occur in the individual. The present invention provides improved compositions, products and methods for locally treating bone fractures, fissures, splintering and similar breakages of the bone, or by strengthening decomposed bone tissue by increasing the mechanism of mineralization of the bone. It is conceivable that the current invention also causes mineralization of the surrounding connective tissue, such as collagen, cartilage, tendons, ligaments and other dense connective tissue and reticular fibers.

The Oral Cavity

With respect to tissue decomposition in the oral cavity, it is commonly known in the dental art that certain kinds of tooth decomposition and decay that occurs over time in the mouth is initiated by acid etching of the tooth enamel with the source of the acid being a metabolite resulting from bacterial and enzymatic action on food particles in the oral cavity. It is generally understood that plaque, a soft accumulation on the tooth surface consisting of an organized structure of microorganisms, proteinaceous and carbohydrate substances, epithelial cells, and food debris, is a contributory factor in the development of various pathological conditions of the teeth and soft tissue of the oral cavity. The saccharolytic organisms of the oral cavity which are associated with the plaque, cause a demineralization or decalcification of the tooth beneath the plaque matrix through metabolic activity which results in the accumulation and localized concentration of organic acids. The etching and demineralization of the enamel may continue until they cause the formation of dental caries and periodontal disease within the oral cavity.

Teeth are cycled through periods of mineral loss and repair also as a result of pH fluctuations in the oral cavity. The overall loss or gain of mineral at a given tooth location determine whether the carious process will regress, stabilize or advance to an irreversible state. Numerous interrelated patient factors affect the balance between the remineralization and demineralization portions of this cycle and include oral hygiene, diet, and the quantity and quality of saliva. At the most extreme point in this process, a restoration will be required to repair the tooth.

Methods for the prevention and reduction of plaque and tooth decay within the oral cavity commonly involve the brushing of the teeth using toothpastes; mechanical removal of the plaque with dental floss; administration and rinsing of the oral cavity with mouthwashes, dentifrices, and antiseptics; remineralization and whitening of the teeth with fluoride agents, calcium agents and whitening agents, and various other applications to the oral cavity. Still missing in the field is a delivery system for the remineralization of teeth that would address the challenges of demineralization facing the teeth continually in the oral cavity.

A tooth that has reached an advanced stage of decay often requires installation of a dental restoration within the mouth. Half of all dental restorations fail within 10 years, and replacing them consumes 60% of the average dentist's practice time. Current dental materials are challenged by the harsh mechanical and chemical environment of the oral cavity with secondary decay being the major cause of failure. Development of stronger and longer-lasting biocompatible dental restorations by engineering novel dental materials or new resin systems, enhancing existing materials, and incorporating bioactive agents in materials to combat microbial destruction and to sustain the harsh mechanical and chemical environment of the oral cavity continues to be desired.

Despite numerous preventive oral health strategies, dental caries remains a significant oral health problem. More than 50% of children aged 6-8 will have dental caries and over 80% of adolescents over age 17 will have experienced the disease. Caries is also seen in adults both as a primary disease and as recurrent disease in already treated teeth. Advances in diagnosis and treatment have led to non-invasive remineralizing techniques to treat caries. However mechanical removal of diseased hard tissue and restoration and replacement of enamel and dentin is still the most widely employed clinical strategy for treating primary caries, restoring function to the tooth and also blocking further decay. In addition, nearly 50% of newly placed restorations are replacement of failed restorations. Clearly, restorative materials are a key component of treating this widespread disease.

The selection of a restorative material has significantly changed in recent years. While dental amalgam is still considered a cost effective material, there is a growing demand for tooth colored alternatives that will provide the same clinical longevity that is enjoyed by dental amalgam. The use of composite resins has grown significantly internationally as a material of choice for replacing amalgam as a restorative material for posterior restorations. This demand is partially consumer driven by preference for esthetic materials and the concerns regarding the mercury content of amalgam. It is also driven by dentists recognizing the promise of resin-based bonded materials in preserving and even supporting tooth structure. Numerous studies have suggested that bonding the restoration to the remaining tooth structure decreases fracture of multi-surface permanent molar preparations. Unfortunately, posterior teeth restored with direct resin restorative materials have a higher incidence of secondary caries. This has led to shorter clinical service and narrower clinical indications for composite resin materials compared to amalgam.

The most frequently cited reason for restoration replacement is recurrent decay around or adjacent to an existing restoration. It is likely that fracture at the margin due to polymerization shrinkage can lead to a clinical environment at the interface between a restoration and the tooth that collects dental plaque and thus promotes decay. Therefore, developing dental materials with anti-caries capability is a very high priority for extending the longevity of restorations.

Tooth Remineralization

Although natural remineralization is always taking place in the oral cavity, the level of activity varies according to conditions in the mouth as discussed. Incorporation of fluoride during the remineralization process has been a keystone for caries prevention. The effectiveness of fluoride release from various delivery platforms, including certain dental restorative materials has been widely demonstrated. It is commonly accepted that caries prevention from fluoride is derived from its incorporation as fluorapatite or fluoride enriched hydroxyapatite in the tooth mineral thereby decreasing the solubility of tooth enamel. More recently, anti-caries activity has been demonstrated using the strategy of increasing solution calcium and phosphate concentrations to levels that exceed the ambient concentration in oral fluids. In order for fluoride to be effective at remineralizing previously demineralized enamel, a sufficient amount of calcium and phosphate ions must be available. For every two (2) fluoride ions, ten (10) calcium ions and six (6) phosphate ions are required to form a cell of fluorapatite $(Ca_{10}(PO_4)_6F_2)$. Thus the limiting factor for net enamel remineralization is the availability of calcium and fluoride in saliva.

The low solubility of calcium phosphates has limited their use in clinical delivery platforms, especially when in the presence of fluoride ions. These insoluble phosphates can only produce available ions for diffusion into the enamel in an acidic environment. They do not effectively localize to the tooth surface and are difficult to apply in clinically usable forms. Because of their intrinsic solubility, soluble calcium and phosphate ions can only be used at very low concentrations. Thus they do not produce concentration gradients that drive diffusion into the subsurface enamel of the tooth. The solubility challenge is exacerbated by the even lower solubility of calcium fluoride phosphates.

Several commercially available approaches exist using calcium and phosphate preparations that have been commercialized into various dental delivery models. These have been reportedly compounded to overcome the limited bioavailability of calcium and phosphate ions for the remineralization process. The first technology uses casein phosphopeptide (CCP) stabilized with amorphous calcium phosphate (ACP) (RECALDENT® CCP-ACP of Cadbury Enterprises Pte. Ltd.). It is hypothesized that the casein phosphopeptide can facilitate the stabilization of high concentrations of ionically available calcium and phosphate even in the presence of fluoride. This formulation binds to pellicle and plaque and while the casein phosphopeptide prevents the formation of dental calculus, the ions are available to diffuse down the concentration gradient to subsurface enamel lesions facilitating remineralization. As compared to the CCP-ACP, in the composition of the invention, biologically available ions are available due to the fact that the salts are already solvated in the microcapsule of the invention. Amorphous calcium phosphate is not soluble in water or saliva. Although the manufacturer claims release of bioavailable ions from amorphous calcium phosphate, it is not as a result of the dissolution of the complex. A second technology (ENAMELON®) uses unstabilized amorphous calcium phosphate. Calcium ions and phosphate ions are introduced as a dentifrice separately in a dual chamber device forming amorphous calcium phosphate in-situ. It is proposed that formation of the amorphous complex promotes remineralization. A third approach uses a so-called bioactive glass (NOVAMIN® of NovaMin Technology Inc.) containing calcium sodium phosphosilicate. It is proposed that the glass releases calcium and phosphate ions that are available to promote remineralization. More recently dental composite formulations have been compounded using zirconia-hybridized ACP that may have the potential for facilitating clinical remineralization.

While the Recaldent® and Enamelon® preparations have both in-situ and in-vivo evidence suggesting enhanced remineralization, these are topically applied and do not specifically target the most at risk location for recurrent caries at the tooth restoration interface. While the bioactive glass and the zirconia-hybridized-ACP filler technologies have potential, they are relatively inflexible in terms of the range of formulations in which they might be used due to the challenges of dealing with brittle fillers and some of the limitations on controlling filler particle size.

Another approach taken to decrease caries in the oral cavity is the limiting of demineralization of enamel and bone by drinking water fluoridation. It has been shown that the fluoride contained in drinking water incorporates to some extent into hydroxyapatite, the major inorganic component of enamel and bone. Fluoridated hydroxyapatite is less susceptible to demineralization by acids and is thus seen to resist the degradation forces of acidic plaque and pocket metabolites. In addition, fluoride ion concentration in saliva is increased through consumption of fluoridated drinking water. Saliva thus serves as an additional fluoride ion reservoir and in combination with buffering salts naturally found in salivary fluid, fluoride ions are actively exchanged on the enamel surface, further offsetting the effects of demineralizing acid metabolites.

Notwithstanding the established benefits of fluoride treatment of teeth, fluoride ion treatment can result in irregular spotting or blotching of the teeth depending on the individual, whether administered through drinking water or by topically applied fluoride treatment. This effect is known to be both concentration related and patient specific. In addition, the toxicology of fluoride is being studied as to its long term effect on human health. Desired is a targeted approach of fluoridation in the oral cavity.

Another approach to limiting the proliferation of microflora in the oral environment is through topical or systematic application of broad-spectrum antibacterial compounds. Reducing the number of oral microflora in the mouth results in a direct reduction or elimination of plaque and pocket accumulation together with their damaging acidic metabolite production. The major drawback to this particular approach is that a wide variety of benign or beneficial strains of bacteria are found in the oral environment which may be killed by the same antibacterial compounds in the same manner as the harmful strains. In addition, treatment with antibacterial compounds may select for certain bacterial and fungi, which may then become resistant to the antibacterial compound administered and thus proliferate, unrestrained by the symbiotic forces of a properly balanced microflora population. Thus the application or administration of broad-spectrum antibiotics alone is ill-advised for the treatment of caries and a more specific, targeted approach is desired.

Tooth Whitening

Cosmetic dental whitening or bleaching has become extremely desirable to the general public. Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as eating, chewing, or drinking certain foods and beverages (in particular coffee, tea, and red wine) and smoking or other oral use of tobacco products cause undesirable staining of surfaces of teeth. Extrinsic staining of the acquired pellicle arises as a result of compounds such as tannins and polyphenolic compounds which become trapped in and tightly bound to the proteinaceous layer on the surfaces of teeth. This type of staining can usually be removed by mechanical methods of tooth cleaning. In contrast, intrinsic staining occurs when staining compounds penetrate the enamel and even the dentin or arise from sources within the tooth. The chromogens or color causing substances in these materials become part of the pellicle layer and can permeate the enamel layer. Even with regular brushing and flossing, years of chromogen accumulation can impart noticeable tooth discoloration. Intrinsic staining can also result from microbial activity, including that associated with dental plaque. This type of staining is not amenable to mechanical methods of tooth cleaning and chemical methods are required.

Without specifically defining the mechanism of action of the present invention, the compositions, products and methods of the present invention enable the precipitation of salts onto the surfaces of the teeth in the oral cavity and make the salts available for adherence to the tooth surface and remineralization of the teeth. The mineralizing salts are deposited in the interstitial spaces of the teeth, making the teeth smoother, increasing the reflection of light from the surface of the teeth and thereby giving the teeth a brighter, more lustrous appearance and whiter visual effect.

Tooth whitening compositions generally fall into two categories: (1) gels, pastes, varnishes or liquids, including toothpastes that are mechanically agitated at the stained tooth surface in order to affect tooth stain removal through abrasive erosion of stained acquired pellicle; and (2) gels, pastes, varnishes or liquids that accomplish the tooth whitening effect by a chemical process while in contact with the stained tooth surface for a specified period, after which the formulation is removed. In some cases, the mechanical process is supplemented by an auxiliary chemical process which may be oxidative or enzymatic. Initially, tooth whitening had been performed at the dentist's office. Less expensive at-home dental whitening kits have become available, such as whitening strips and whitening trays that come in either single compartment or dual compartment systems.

Both in-office and at-home tooth whitening typically involves the application of a peroxide containing composition to the surface of the tooth to achieve the desired whitening effect. The majority of most in-office and at-home tooth whitening compositions act by oxidation. These compositions are applied directly by a patient in a tooth-bleaching tray, held in place in the mouth for contact times, sometimes for periods of half an hour several times per day; or of greater than 60 minutes per day, and sometimes as long as 8 to 12 hours. The slow rate of bleaching is, in large part, the consequence of formulations that are developed to maintain stability of the oxidizing composition. Aqueous tooth whitening gels have proven desirable due to the hydrating effects on the structure of the tooth, reducing the likelihood of tooth sensitivity.

The most commonly used oxidative compositions contain the hydrogen peroxide precursor carbamide peroxide which is mixed with an anhydrous or low-water content, hygroscopic viscous carrier containing glycerine and/or propylene glycol and/or polyethylene glycol. When contacted by water, carbamide peroxide dissociates into urea and hydrogen peroxide. The latter has become the tooth bleaching material of choice due to its ability to whiten teeth faster than higher concentrations of carbamide peroxide.

An alternative source of hydrogen peroxide is sodium percarbonate and this has been used in a silicone polymer product that is painted onto the teeth forming a durable film for overnight bleaching procedures. The peroxide is slowly released for up to 4 hours.

Associated with the slow rate of bleaching-in the hygroscopic carrier, the currently available tooth-bleaching compositions cause tooth sensitization in over 50% of patients. Tooth sensitivity is believed to result from the movement of fluid through the dentinal tubes toward nerve endings in the tooth. This movement is enhanced by the carriers for the carbamide peroxide. It has been determined that glycerine, propylene glycol and polyethylene glycol can each give rise to varying amounts of tooth sensitivity following exposure of the teeth to heat, cold, overly sweet substances, and other causative agents.

Hydrogen peroxide tooth bleaching formulations have limitations in addition to tooth sensitivity. Until recent years, stable aqueous hydrogen peroxide tooth bleaching gels have been virtually non-existent. Hydrogen peroxide is a powerful oxidizing agent and an unstable compound that decomposes readily over time into water and oxygen. Certain chemical and physical influences in the oral cavity can accelerate the rate of decomposition and need to be controlled for a stable tooth whitening gel to exist. Temperature, pH and errant metal ions all have a profound effect on the decomposition of hydrogen peroxide, particularly in an aqueous formula.

One advantage of the compositions of the invention is the decrease or elimination of tooth sensitivity of the patient. When used in conjunction with current tooth bleaching products, the microcapsules of the invention release salt ions that precipitate as salts in the oral cavity and mineralize the open dentin tubules of the teeth thereby decreasing tooth sensitivity to the oxidative tooth bleaching product.

Whitening systems on the market include two-part systems that require mixing of the components upon administration and single part compositions that are faster and easier to administer and generally preferred for in-office bleaching by dentists. Two-part systems include products such as dual barrel syringes, liquid hydrogen peroxide/powder systems and whitening strips. Single component tooth bleaching compositions prefer room temperature storage conditions in order to eliminate costly and inconvenient storage problems. The pH of an aqueous hydrogen peroxide tooth whitening composition also has great bearing on the stability of the formulation. The two-part systems demonstrate superior shelf life stability. Formulations that contain hydrogen peroxide solutions are strongly acidic and maintain their stability in acidic pH formulas. Stable aqueous hydrogen peroxide tooth whitening gels can be formulated in the acid pH range. However, bleaching compositions in the acidic pH range (pH 2.0-5.5) are prone to the demineralization of dental enamel by the solubilizing of calcium ions from the tooth surface. This reduction in surface enamel leads to tooth sensitivity and discomfort for the patient. By incorporating the compositions of the invention into tooth bleaching products or utilizing them in conjunction with tooth bleaching products, the microcapsules of the invention can modify the pH level in the oral cavity to cause acceleration of the bleaching process.

Many of the available products are time-consuming and limited in their effectiveness and subject the user to various physical discomforts. More importantly, it has been shown that prolonged exposure of teeth to whitening compositions, as practiced at present, has a number of adverse effects in addition to that of tooth sensitivity. Over time, any of the peroxides known in the art to achieve a desired tooth bleaching effect will function as calcium chelating agents. Other examples of chelation agents often found in tooth whitening products include EDTA and its salts, citric acid and its salts, gluconic acid and its salts, alkali metal pyrophosphates and alkali metal polyphosphates. Solubilization of calcium from the enamel layer can occur at a pH less than 5.5 with associated demineralization. The chelating agents will penetrate the intact enamel and dentin so as to reach the pulp chamber of a vital tooth thereby risking damage to pulpal tissue. Other adverse effects include dilution of the bleaching compositions with saliva in the oral cavity with resulting leaching from the dental tray and subsequent digestion by the user.

It has been shown that the rate of whitening can be increased by increasing the temperature of the hydrogen peroxide system, where increase of 10° C. can double the rate of reaction. Consequently, there exist a number of procedures that utilize high-intensity light to raise the temperature of the hydrogen peroxide to accelerate the rate of bleaching of the teeth. Other approaches to heating the hydrogen peroxide have been described such as the heating of dental instruments. Contemporary approaches and literature have focused on accelerating peroxide bleaching with simultaneous illumination of the anterior teeth with various sources having a range of wavelengths and spectral power, for example, halogen curing lights, plasma arc lamps, lasers and light-emitting diodes. Some products that are used in light activated whitening procedures contain ingredients that serve as photosensitizers that claim to aid the energy transfer from the light to the peroxide gel and are often colored materials, for example carotene and manganese sulfate. However, excessive heating can cause irreversible damage to the dental pulp. In addition, the literature for in vitro and clinical studies and actual results demonstrate that the actual effect of light on tooth whitening is limited, conflicting and controversial.

There is thus a need for improved compositions, methods and products that overcome the limitations of the prior art. The challenge remains to create a tooth whitening and remineralization technology platform for incorporating stable and effective tissue remineralization ions that can be incorporated into a myriad of dental materials and variety of products. Such a delivery platform would facilitate the formulation of dental products capable of remineralization of the teeth. The compositions, products and methods of the current inventions as described herein satisfy these and other needs. The ultimate impact is a reduction in recurrent caries, the most prevalent reason for restoration replacement; whitening of the teeth; and resulting improvement in overall strength and health of the teeth in the oral cavity.

SUMMARY OF THE INVENTION

In accordance with the description herein and desire to provide an improved tissue and bone mineralization and tooth remineralization products, the present invention provides compositions and methods that increase tissue mineral content and tissue mineral density. Also presented are methods for utilizing such compositions in the treatment and prevention of a wide variety of conditions resulting from tissue decomposition. The invention also provides dental compositions and products for remineralization and whitening of teeth. More particularly, the present invention provides a composition comprising salt solutions encapsulated in a semi-permeable polymer shell that allows the release of biologically available ions to be delivered to mineralized tissue. The microcapsules can be incorporated into a variety of bone restoration and dental products. The microcapsules can be prepared by any generally known microencapsulation methods, but preferably by surfactant free inverse emulsion. More particularly, the invention is a composition containing polymer microencapsulated aqueous solutions of salts of calcium, phosphate, fluoride and combinations and mixtures thereof. Further, the rate of release of the salt ions from the microcapsules can be designed in a single type of microcapsule and in a product containing a number of different types of microcapsules so as to deliver an application with controlled time release of the ions and thereby cause tissue mineralization effect over a prolonged period of time.

DESCRIPTION OF THE DRAWINGS

FIG. 1 is an optical microscope photograph of microcapsules of the invention containing an aqueous 0.1 M $Ca(NO_3)_2$ solution suspended in methyl benzoate.

DETAILED DESCRIPTION OF THE INVENTION

Microencapsulation

In a preferred embodiment, the composition of the invention is formed by combining water, salt, oil-soluble emulsifying agent and at least one type of polymer which combined and upon mixing or agitation form the microcapsules of the invention. For purposes of definition, as used herein, the term "microcapsules" refers to tiny particles or droplets surrounded by a coating to give small capsules having useful properties. Microcapsules are sometimes referred to as microspheres, though a microcapsule of the invention need not be spherical in shape. The material inside the microcapsule shall be referred to herein as the "core" or "internal phase", and the material surrounding the core is meant to connote a "shell", "wall", "coating", "membrane", or "exterior phase." The shell need not be completely or uniformly coated around the core of the microcapsule, as long as substantially most of the core is coated with a polymer shell as will be described further herein.

Preferably, the microcapsules of the invention will have a diameter range of between 100 nanometers and 3 millimeters. More preferably, the size of the microcapsules is between 1 micron and 1 mm. In general, the preferable size of the microcapsule will be governed by the desired end use application. One parameter used to control the size of the microcapsules is by the amount and force of mixing or agitation of the emulsion. Other parameters to control the size of the microcapsules and components of the microcapsules will be discussed further below. The size of the microcapsules of the invention can be optimized so that a sufficient number of microcapsules can be available at the surface of the solid phase of the matrix to be in contact with the tissue, bone or tooth material interface in order to affect mineralization.

Various methods of encapsulation are known for producing microencapsulated particles, though none of the methods have heretofore been applied to the formation of tissue or bone mineralization or dental remineralization compositions as contemplated by the invention. Methods for constructing microcapsules may be physical or chemical. Physical methods of manufacturing include pan coating, air-suspension coating, centrifugal extrusion, vibrational nozzle and spray-drying. Chemical methods of manufacturing include polymerization such as interfacial polymerization, in-situ polymerization and matrix polymerization. In interfacial polymerization, at least two monomers are dissolved separately in immiscible liquids. Upon interface between the liquids, rapid reaction occurs creating a thin shell or wall of the microcapsule. In-situ polymerization is the direct polymerization of a single monomer carried out on the particle surface. In matrix polymerization, a core material is imbedded during formation of the microcapsule. Microcapsules might also be constructed by using sol-gel techniques, by aqueous or organic solution precipitation synthesis methods, complex coacervation, and by other methods known in the art.

A preferred method of preparing the microcapsules of the invention is a synthesis developed herein to generate microcapsules containing aqueous solutions of salts, and in particular, water-soluble calcium, phosphate and fluoride ion-containing salts. In order to encapsulate an aqueous solution of ions in a microcapsule, a surfactant free inverse emulsion of water in oil is preferably used. Any continuous oil phase can be utilized for the process of the invention. In one embodiment of a dental material, hydrophobic oils are utilized as the continuous oil phase within the process with an emulsifying agent that serves to sterically stabilize the dispersed phase. One preferred oil phase of the invention is methyl benzoate. FIG. 1 is an optical microscope photograph of microcapsules of the invention containing an aqueous 0.1 M $Ca(NO_3)_2$ solution suspended in methyl benzoate.

A standard emulsion formally uses a surfactant to stabilize a dispersed droplet; whereas, the present preferred method uses an emulsifying agent in a continuous oil phase to sterically stabilize the dispersed water droplets in order to allow an interfacial polymerization to occur. This causes an effective synthesis of polymer shells around the aqueous ionic solutions in the dispersed phase. The amphiphilic character of surfactants causes interference with the polymerization that needs to occur at the interface of the dispersed phase and the continuous phase that is necessary to generate a capsule. A surfactant also presents a problem in its affinity for ions. The polar hydrophilic head group will be attracted to the ions contained in the capsule for remineralization. The presence of a surfactant decreases the percentage of ions that are truly bioavailable, effectively behaving as a chelation agent inactivating the release of the ions from the capsule. Consequently, surfactant free inverse emulsion interfacial polymerization is preferred as the method for the formation of dental microcapsules of the invention.

Emulsifying Agents

The emulsifying agents preferred in the dental microcapsules of the invention are different from surfactants in that the emulsifying agent exclusively partition into the oil phase and are not surface active. Inherent in the concept of using surfactant free inverse emulsions is that water droplets can be disrupted into small droplets, the size and size distribution of which are dependent on the form and amount of input energy, and the droplets formed survive transiently due to a rather sluggish growth rate. Although surfactant free emulsions have been frequently applied in solvent extraction, emulsion polymerization, food production such as oil-and-vinegar dressing production, very little attention has been paid to its fundamental properties for use in microencapsulation of aqueous biologically active systems. The emulsifying agent sterically stabilizes droplets without interfering with interfacial polymerization. Chelation of remineralization ions is thereby minimized.

Polymers

The microcapsules of the invention contain a shell comprised of at least one polymer, preferably with the shell being semi-permeable to particular aqueous salt solutions. As used herein, the terms "polymer" and "polymers" are intended to connote precursor polymer molecules having a preferable size in the range of 1,000 to 50,000 gram/mole; more preferably from 1,500 to 20,000 g/mole; and more preferably from 1,500 to 8,000 g/mole. Larger polymers can be used, as well as smaller oligomers or pre-polymers, but the molecular weight of the polymer is controlled for practical uses in the desired dental product applications. Conceivably, monomers can be used as well in the method of the invention. A number of polymers can be combined into one microcapsule in order to produce an end use product having particularly desired release characteristics of the core components.

In one embodiment of the invention, the microcapsules shell is designed with limited or substantially no permeability depending on its desired application. The impermeable shell is formed during synthesis by selecting particular polymers known to be impermeable to the particular ions in the desired end use application. Such microcapsules may, for example, be synthesized for "burst" application as will be discussed herein below.

Many classes of polymers can be utilized in the scope of the invention and the choice depends on the specific desired properties. Examples include, but are not limited to: acrylic polymers, alkyd resins, aminoplasts, coumarone-indene resins, epoxy resins, fluoropolymers, phenolic resins, polyacetals, polyacetylenes, polyacrylics, polyalkylenes, polyalkenylenes, polyalkynylenes, polyamic acids, polyamides, polyamines, polyanhydrides, polyarylenealkenylenes, polyarylenealkylenes, polyarylenes, polyazomethines, polybenzimidazoles, polybenzothiazoles, polybenzoxazinones, polybenzoxazoles, polybenzyls, polycarbodiimides, polycarbonates, polycarboranes, polycarbosilanes, polycyanurates, polydienes, polyester-polyurethanes, polyesters, polyetheretherketones, amphiphilic polyurethane polyetherpolyurethanes, polyethers, polyhydrazides, polyimidazoles, polyimides, polyimines, polyisocyanurates, polyketones, polyolefins, polyoxadiazoles, polyoxides, polyoxyalkylenes, polyoxyarylenes, polyoxymethylenes, polyoxyphenylenes, polyphenyls, polyphosphazenes, polypyrroles, polypyrrones, polyquinolines, polyquinoxalines, plysilanes, polysilazanes, polysiloxanes, polysilsesquioxanes, polysulfides, polysulfonamides, polysulfones, polythiazoles, polythioalkylenes, polythioarylenes, polythioethers, polythiomethylenes, polythiophenylenes, polyureas, polyurethanes, polyvinyl acetals, polyvinyl butyrals, polyvinyl formals. One skilled in the art will further appreciate that the selection of the specific type of polymer will impact the composition and permeability characteristics of the microcapsules of the invention.

Salts

For tissue and, particularly for dental applications, fluoride salts, calcium salts and phosphate salts are preferred in the composition of the invention, though other salts may be utilized depending on a desired application. Examples of calcium salts include, but are not limited to, calcium acetate, calcium aluminosilicate, calcium benzoate, calcium bromide, calcium butyrate, calcium aragonite, calcium calcite, calcium chloride, calcium aluminate, calcium chloride fluoride orthophosphate, calcium thiosulfate, calcium valerate, calcium cinnamate, calcium citrate, calcium fluosilicate, calcium fluoride, calcium formate, calcium fumarate, calcium gluconate, calcium glycerophosphate, calcium iodate, calcium iodide, calcium isobutyrate, calcium lactate, calcium lysinate, calcium malate, calcium malonate, calcium nitrate, calcium-1-phenol-4-sulfonate, calcium orthophosphate, calcium pyrophosphate, calcium propionate, calcium salicylate, calcium quinate, calcium orthosilicates, calcium tartrate, calcium sulfate, and calcium thiocyanate. Examples of sodium salts, fluorine-providing salts include, but are not limited to sodium fluoride, fluorosilicic acid, sodium fluorosilicate, sodium monofluorophosphate, sodium silicofluoride, potassium fluoride, cuprous fluoride, tin fluoride such as stannous fluoride or stannous chlorofluoride, ammonium fluorosilicate, alumina mono- and difluorophosphate. Examples of phosphate salts include, but are not limited to, potassium phosphates, sodium phosphates, and magnesium phosphate.

In one preferred embodiment of the method of the surfactant free inverse emulsion polymerization of the invention, a very low molecular weight polyurethane is premixed into the continuous oil phase. Preferably the molecular weight of the polyurethane is 1,500 to 20,000 g/mole, and more preferably from 1,500 to 8,000 g/mole. Due to the amphiphilic nature of the low molecular weight polyurethane, the polyurethane spends the majority of the time at the interface of the dispersed and continuous phases.

In said embodiment, diol is added to the system to increase the molecular weight of an isocyanate functionalized polyurethane shell. A preferred diol is ethylene glycol. The diol ultimately leads to ethylene oxide linker units in the microcapsule chemical structure. It has been shown in industrial applications that ethylene oxide does not inhibit the flow of ions between electrodes. This approach is useful for understanding the structure property relationship of the urethane on permeability of the microcapsules due to the ease with which the chemical structure can be varied in the synthesis of the microcapsules by simply changing the identity of the diol used in the polyurethane wall of the microcapsule. In this embodiment, the ion permeability of the microcapsule shell of the composition is based on the chemical composition of the diols that act as spacer monomers used in the synthesis of the microcapsule. The following scheme represents the reaction used to synthesize the microcapsule shell of this embodiment:

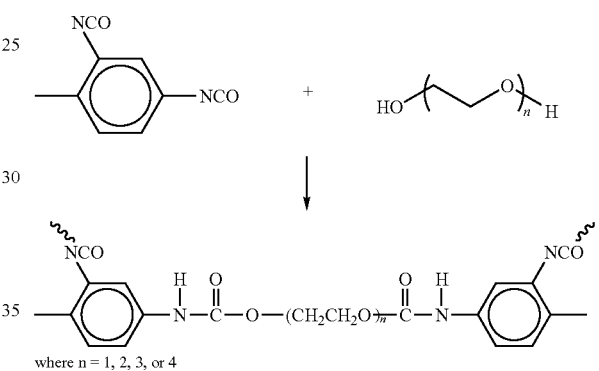

where n = 1, 2, 3, or 4

The length of the ethylene oxide spacer in the microcapsule wall may be varied in order to control ion permeability of the membrane shell. Preferred embodiments include microcapsules using ethylene glycol (n=1) and from 1,4-butanediol (n=2). Preferred embodiments include microcapsules from diols where n=3 (1,6-hexanediol) or 4 (1,8-octanediol).

A second characteristic influencing the ion permeability of the microcapsule membrane is the shell or wall thickness, which may be varied by varying the ratio of the mass of material used to synthesize the shell to the volume of the dispersed aqueous ionic salt solution. At a constant stir rate, adding more material relative to the aqueous ionic phase will lead to formation of thicker microcapsule walls. In a preferred embodiment, the invention comprises a ratio of 1 gram of polyurethane to from 15 to 40 mL of aqueous solution.

Microencapsulation of specific remineralizing ions allows all constituents to be incorporated into a single phase without the need to separate the various reactive ions by means of a physical barrier, such as the dual barrel syringe, dual bladder tube, or the two separate container systems of tooth whitening products. The method of the invention permits incorporation of discrete and isolated microcapsules of reactive remineralizing ions into aqueous systems. This single phase of an aqueous dental composition precludes the need for special designs for binary containers and enables prolonged stability of the finished dental product until needed. Preferred specific embodiments of such dental compositions include products that have immediate application to the oral cavity such as single phase dentifrices, mouth rinses, whitening pastes, gels, liquids and varnishes and whitening strips. The combined use of these particular remineralizing ions in a single phase in aqueous systems is presently not feasible.

Embodiments of the dental materials of the invention can be formulated such that only one type of mineralization ion is contained within the core of the microcapsule or alternatively, a plurality of different types of salts, and thereby salt ions, can be incorporated into one microcapsule.

In other embodiments, a plurality of microcapsules containing one type of ion can be combined in a product with microcapsules containing other ions. For example, microcapsules having calcium salts are combined in a mouth rinse product also containing microcapsules containing phosphate salts. The calcium and phosphate ions will be released into the oral cavity via permeation through the shell membranes of the microcapsules or by bursting of the microcapsules in the mouth. Upon release, the calcium and phosphate salt ions will form amorphous calcium phosphate which will precipitate from the saliva and cause remineralization of the teeth. Another example of a product may be a mouth rinse containing calcium salts, phosphate salts and fluoride salts, each in separate microcapsules, which may be semi-permeable or non-permeable. By rinsing of the mouth, the microcapsules will burst open to release the salt ions which, when combined in the oral cavity will form and precipitate onto the teeth as calcium fluoride and amorphous calcium phosphate fluoride.

Controlled Release

The microcapsules and products of the invention can be designed to have different time release profiles, in such a way as to permit controlled time release, also known as sustained release or long-term release, of the specific ions or constituents to effectuate various desired results. Thus, various salt ions or components of the invention can be released at varying periods of time from each microcapsule.

Furthermore, the ratios of release times in different types of microcapsules can be incorporated into the design of a single product to optimize the permeability and concentration of the specific ions or constituents of each type of microcapsule in the product relative to one another and relative to the environment where they are required. Such design enables a mineralization product that can deliver a number of active ingredients over a controlled time to a particular site of tissue decomposition without the need for numerous administrations of a product to a patient and thereby minimizing the treatment regiment of the patient.

For example, a dental product can remineralize the area of a tooth material in contact with the dental composition in order to prevent caries, whiten the teeth and/or provide an antibacterial treatment to a targeted tooth surface in the oral cavity. For example, fillings, sealants and cements can be designed to contain the controlled release microcapsules of the invention and to release salt ions over time to the area of contact with the tooth or tooth material. Sustained release dosage forms of dental products will avoid the necessity of frequent administration of an active while at the same time achieving a desired level of remineralization or whitening in the oral cavity.

One method by which controlled release design can be effectuated is by specific selection or composition of the shell polymer having desired permeability within the shell. Another method to control permeability and release profile is to control the thickness of the shell layer during synthesis of the microcapsules as described herein.

Ion concentration within the microcapsule can also be varied to effect permeability. In a preferred embodiment, biologically active $Ca^{2+}$, $PO_4^-$ and $F^-$ ions and combinations thereof may be incorporated in the microcapsules. Each microcapsule is synthesized with an aqueous solution of a salt with a specific targeted ion over a range of concentrations. Salts with a high solubility in water are preferred but not necessarily required. Preferred embodiments include $Ca(NO_3)_2$, $K_2HPO_4$, and NaF. Preferred embodiments include microcapsules with a range of molarities that reflect a percentage of saturation of the given ion from 5 to 95%; more preferably from 25 to 95%, and more preferably from 70 to 90%. Table 1 sets forth several preferred embodiments.

TABLE 1

| Ion Permeable Microcapsule as a source of: | Ion Source | Concentration | | Microcapsule Wall Thickness (µm) | Monomer Variation HO—$(CH_2CH_2O)_n$—H |
| --- | --- | --- | --- | --- | --- |
| | | Saturation Percentage | Molarity | | |
| Calcium | $Ca(NO_3)_2$ | 25-95% | 1.8-6.9 | 5-25 | n = 1, 2, 3, 4 |
| Phosphate | $K_2HPO_4$ | 25-95% | 2.2-8.7 | 5-25 | n = 1, 2, 3, 4 |
| Fluoride | NaF | 25-95% | 0.2-0.9 | 5-25 | n = 1, 2, 3, 4 |

For example, tablets comprising the microcapsules of the invention can be produced from which the active ingredient is not all immediately absorbed, but the active ingredient is released gradually and continuously over a period of time from administration.

In the oral cavity, an instant release or "burst" release of the microcapsules can result upon mechanical agitation of the teeth, such as by use of toothbrushes or dental floss in the oral cavity; by regular chewing, grinding, gritting, clenching or clamping of the teeth or gums; by tongue motion or pressure of the tongue; or by swishing or gargling of liquids by the jaw muscles and motion of other muscles within the internal orifices of the mouth. Both semi-permeable microcapsules and the impermeable microcapsules of the invention, as described above, can be incorporated into products designed for burst release effect.

Loading of the Microcapsules

The microcapsules of the invention contain semi-permeable polymer shells wherein the permeability functions to release salt ions both out of the microcapsules and into the microcapsules from the surrounding environment as a result of concentration gradients. Thus, embodiments are contemplated where already formed microcapsules having none or less than the maximum possible amount of aqueous salt solution in the core can be charged with additional salt solution or salt ions, herein referred to as "loading." Loading also includes "recharging" of empty microcapsules in the presence of reactive ions and appropriate concentration gradients. The new ions can be introduced into the core of partially loaded microcapsules or reintroduced into the core of empty microcapsules by immersing the microcapsules into highly mineralized charged salt solutions where the concentration of salt ions in the salt solution is higher than the concentration of salt ions within the core of the microcapsules.

Embodiment of rechargeable applications of the invention include products such as dental resins and cements that are maintained in the oral cavity over a relatively lengthy period of time and can thereby be utilized to remineralize, fluoridate or whiten the teeth. The recharge rate of the microcapsules will depend on the concentration gradients of the salt ions and the release profile of the particular polymers of the product.

Bone Restorative Materials

The compositions of the invention are useful in a variety of bone restorative or regeneration products. There is a need for new materials that can stimulate the body's own regenerative mechanisms and heal tissues. Porous templates that act as scaffolds are thought to be required for three-dimensional bone tissue growth. It has recently been discovered that bioactive glass have high potential as scaffold materials as they stimulate bone-forming cells to produce new bone, they are degradable in the body and they bond to bone.

In an example, a study with a three dimensional polycaprolactone tricalcium phosphate bone composite scaffold was evaluated for applications in bone engineering. The bone scaffolds were immersed in simulated body fluids at 37° C. and monitored for weight loss and water absorption. Biochemical assays and microscopy revealed that calcium was deposited on the surface of the scaffolds and caused crystallization of the hydroxyapatite layer of the scaffold. The microcapsules of the invention can be incorporated into such and similar bioactive bone scaffolds in order to initiate or augment the formation of bone and cause bone regeneration. (See, Y. Lei, B. Rai, K. H. Ho and S. H. Teoh, In vitro degradation of novel bioactive polycaprolactone—20% tricalcium phosphate composite scaffolds for bone engineering, National University of Singapore, 2006).

Uses of bone regeneration products in the dental field include building up of the bone tissue around implants placed in tooth sockets after tooth extraction or preparation for future implantation of false teeth or prosthetics. Another useful application is the filling of bone defects after removing the root of a tooth, cystectomy or the removal of impacted teeth. Yet another application is the reparation of bone defects after the reopening of a wound in the oral cavity.

Dental Products

Specific dental products comprising the microcapsules of the invention include dental gels, pastes, rinses, dentifrices, whitening products, breath fresheners, artificial saliva systems, varnishes, desensitizers and other dental products well known in the dental art. Dental restorative materials include composite and other solid phase filling materials, adhesives and cements, temporary restorative materials, coatings on implants for the induction of bone growth. Various embodiments of the invention include over-the-counter applications such as toothpastes, bleaching agents, varnishes, sealants, sealers, resin restorative materials, glass ionomers (including resin modified glass ionomers), bioactive glass, compomer restorative materials, giomer restorative materials, oral rinses, any topical preventive or remineralizing agents (liquids, gel mousses, pastes), any rinse including antimicrobial agents, professionally applied and over-the-counter "paint-on" liquids gels, varnishes, sealers, indirect laboratory materials including laboratory resins, denture teeth, denture base materials, dental cements, root canal fillers and sealers, materials used for bone grafting, bone cements, dental implant tissue growth materials, endodontic root filling materials (i.e. apicoectomy materials sometimes called retro-fill materials), pulp capping materials, temporary restorative filling materials, prophy paste, periodontal scaling gels, air abrasion powders for prophylaxis, orthodontic cements, oral surgery extraction socket dressing, cadaver bone, and other bone substitutes.

Embodiments of dental products also include products that can dissolve in the oral cavity upon contact with saliva as a result of enzymatic activity in the oral cavity, such as dissolvable whitening strips. Other products incorporating the microcapsules that can effect the remineralization of teeth include chewing gums, candies, lozenges, capsules, tablets and various food items.

In an embodiment where the microencapsulated dental compositions of the specific remineralizing ions of the invention allow incorporation of salt ions into a matrix of polymerizable composites and other solid filling dental restorative materials such as glass ionomer cements, the incorporation of the microencapsulated ions provides a source for bioactive filling materials and adhesives. The use of semi-permeable microcapsules allows the material to release these remineralizing compounds at the interface between the tooth structure and the restorative filling material or adhesive. This interface is particularly vulnerable to bacterial ingress, attack and subsequent secondary caries development. The presence of fluid within this interface can signal possible micro-leakage at the restorative interface but also allow activation of the material to release the required ions in order for the remineralization process to occur. Embodiments of the microcapsules of the invention can be designed to release the salt ions when under mechanical stress at the opening of a space at the tooth/filling interface.

Dental composition embodiments of the invention can also be designed to comprise a solid phase, such as composites, which offer multiple advantages. Presently, it is unknown to add remineralizing ions into a resin composite and provide activity of the ions because the ions are likely incorporated or entombed within the resin or plastic insoluble matrix.

In one preferred practice of the invention, an oral dental product such as a toothpaste, mouthwash or dentifrice containing the microcapsule composition of the present invention is preferably applied regularly to the oral cavity, though regular application is not necessary, such as every day or every second or third day or a few times a day.

In accordance with various embodiments of the present invention, a tooth whitening composition is provided for imparting a natural white appearance to a tooth surface. The tooth surface is generally comprised of enamel, dentin and acquired pellicle and the whitening composition contacts and preferably adheres to the dental surface to impart an immediate discernible whitening effect, thus rapidly altering the color of the surface of the tooth. In certain embodiments, the present invention provides methods for whitening a tooth surface by using compositions of the present invention. The dental product functions as a delivery system that operates to disperse and adhere the salt ions that act as whitening particulates to a tooth surface to provide a natural white appearance. The whitening compositions of the present invention may be applied to the teeth by any suitable means, known in the art of tooth whitening. Examples include application of toothpastes, rinses, gels, extruded forms such as strips, including dissolvable whitening strips, paint-on liquids and varnishes, single and dual compartment products.

Increase in whiteness of a dental surface can be observed visually, for example with the aid of color comparison charts or gauges, or measured by colorimetry, using any suitable instrument such as a Minolta Chromameter, e.g., model CR-400 (Minolta Corp., Ramsey, N.J.). The instrument can be programmed, for example, to measure Hunter Lab values or L*a*b* values according to the standard established by the International Committee of Illumination (CIE). Though there is no one standard in the dental field to measure and determine tooth color, a very common method is the VITA® Shade Guide (Vita® Zahnfarbik, Bad Sackingen, Germany.) The range of shades in the VITA® Shade Guide varies from very light (B1) to very dark (C4). A total of 16 tooth shades constitute the range of colors between these two endpoints on a scale of brightness. Patient satisfaction with a tooth whitening procedure and product increases with the number of tooth shade changes achieved.

Other Additives

In some embodiments, a sweetener is employed in products that incorporate the microcapsule compositions of the present invention. Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptidebased intense sweeteners, cyclamates, dihydrochalcones, and mixtures thereof. One or more sweeteners can be present in a total amount depending strongly on the particular sweetener(s) selected, Products incorporating the compositions of the present invention optionally comprise a flavoring agent in various embodiments. Flavoring agents among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methyl salicylate), peppermint oil, clove oil, bay oil, anise oil, eucalyptus oil, citrus oils, fruit oils and essences including, those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavoring agents are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, a-irisone, propenyl guaiethol, thymol, linalool, benzaldehyde, cinnamaldehyde, N-ethyl-p-menthan-3-carboxamine, N,2,3trimethyl-2-isopropylbutanamide, 3-1-menthoxypropane-1,2-diol, cinnamaldehyde glycerol acetal (CGA), methone glycerol acetal (MGA), and mixtures thereof. One or more flavoring agents can optionally be present in the compositions of the invention.

In various embodiments, an active ingredient is included in products comprising the compositions of the present invention. In some embodiments, the optional active ingredient is a "systemic active" which is operable to treat or prevent a disorder which, in whole or in part, is not a disorder of the oral cavity. In various embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful in the dental compositions herein include anticaries agents, tartar control agents, periodontal actives, abrasives, breath freshening agents, malodour control agents, tooth desensitizers, salivary stimulants, and combinations thereof. It is understood that while general attributes of each of the above categories of actives may differ, there may some common attributes and any given material may serve multiple purposes within two or more of such categories of actives.

Products comprising the compositions of the present invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Products containing compositions of the present invention optionally comprise an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. The products of the invention can optionally comprise a suitable pH adjusting agents, including, but not limited to, sodium hydroxide, potassium hydroxide, and ammonium, for controlling the stability and shelf life of a dental product.

Dental product of the present invention optionally comprise an antiplaque (e.g., plaque disrupting) agent. One or more such agents can be present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

Dental products and pharmaceutical compounds containing the compositions of the present invention optionally comprise an anti-inflammatory agent. One or more such agents can be present in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone.

Dental products incorporating the compositions of the present invention optionally comprise a desensitizing, or tooth sensitivity protecting, agent. One or more such agents can be present. Suitable desensitizing agents include without limitation potassium salts such as potassium citrate, potassium tartrate, potassium chloride, potassium sulfate and potassium nitrate. Another suitable desensitizing agent is sodium nitrate. Alternatively or in addition a local or systemic analgesic such as aspirin, codeine, acetaminophen, sodium salicylate or triethanolamine salicylate can be used.

Products such as food materials incorporating the compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), fish oil (including components thereof such as omega-3 (N-3) polyunsaturated fatty acids, eicosapentaenoic acid and docosahexaenoic acid), coenzyme Q10, and mixtures thereof.

In another embodiment of the invention, the products comprising the microcapsules may further include an antibacterial agent for release onto the bone tissue or dental surface. A wide variety of antimicrobial active compounds may be employed. These actives may generally be classified as halogenated hydrocarbons, quaternary ammonium salts and sulfur compounds. Halogenated hydrocarbons include halogenated derivatives of salicylanilides, carbanilides, bisphenols, diphenyl ethers, anilides of thiophene carboxylic acids and chlorhexidines. Quaternary ammonium compounds include alkyl ammonium, pyridinum, and isoquinolinium salts. Sulfur active compounds include thiuram sulfides and dithiocarbamates.

Other suitable examples include without limitation copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like.

Other suitable antibacterial agents include nonionic and anionic antibacterial agents known to one of skill in the art. Example non-ionic antibacterial agents include the substantially water insoluble, noncationic antibacterial agents such as alkylphenoxy phenols; cycloalkyl-phenoxyphenols; 9,10-dihydrophenanthrenol; alkylphenols; cycloalkyl-phenols; phenolic compounds; halogenated carbanilides; halogenated salicylanilides; benzoic esters; halogenated diphenyl ethers, and mixtures thereof. A particularly suitable non-ionic antibacterial agent is a diphenyl ether such as 2,4,4'-trichloro-2'-hydroxydiphenyl ether (Triclosan) and 2,2'-dihydroxy-5,5'-dibromodiphenyl ether. One or more antimicrobial agents are optionally present in an antimicrobial effective total amount.

In various embodiments of the dental products of the present invention, the dental product comprises an adhesive or adhesion enhancing agent which serves multiple functions, including enhancing adherence of a composition to the surface of the tooth to be remineralized or whitened. The adhesives are optimized for adhering to the teeth, resisting adherence to non-tooth oral surfaces such as the lips, gingival or other mucosal surfaces, and remaining attached to the teeth for an extended time. Optimization of such aspects may be achieved from varying the physical and chemical properties of a single adhesive or combining different adhesives. In certain embodiments of the present invention, the adhesive polymers in the product are those in which a dental particulate can be dispersed and are well known in the art.

The compositions of this invention can also be incorporated into candies, lozenges, chewing gums, tablets, capsules or other products. Incorporation of the microcapsules into the product can be achieved by, for example, stirring into a warm gum base or coating the outer surface of a gum base, illustrative of which may be jelutong, rubber latex, vinylite resins, and similar compounds desirably with conventional plasticizers or softeners, sugar, glucose, sorbitol or other sweeteners. It is also contemplated herein that the microcapsule compositions of the present invention can be incorporated into a variety of food items.

It will be clearly understood that although this specification refers specifically to applications in humans, the invention is also useful for veterinary purposes. Thus, in all aspects, the methods and compositions of the invention are useful for domestic animals such as cattle, sheep, horses and poultry; and for companion animals such as cats and dogs; as well as for other animals.

It will be appreciated by persons skilled in the art that the present invention is not limited to the specific embodiments that have been particularly shown and described hereinabove. Rather the scope of the present invention includes combinations of the features described as well as modifications and variations thereof which would occur to a person of skill in the art upon reading the foregoing description and which are not in the prior art.

EXAMPLES

The following examples set forth the compositions and the synthesis methods of the invention. These experiments demonstrate the feasibility of using the surfactant free interfacial polymerization of a reverse emulsion to successfully encapsulate ionic solutions of salts to create effective tissue mineralization compositions.

Example 1

Synthesis Data

Three microcapsule compositions of the invention were prepared: the first containing aqueous solution of $Ca(NO_3)_2$; the second containing aqueous solution of $K_2HPO_4$; the third, an aqueous solution of NaF, by performing an interfacial polymerization in a stable inverse emulsion of aqueous salt solutions in a methyl benzoate continuous phase. 6 grams of polyglyceryl-3-polyricinoleate (P3P) was used as the emulsifying agent. The emulsifying agent and a 4 grams of polyurethane polymer were mixed together. The aqueous solution of salt (100 mL of one molar potassium phosphate dibasic) was added to 210 mL of continuous methyl benzoate oil phase under mixing. 0.2 g of ethylene glycol was subsequently added to the inverse emulsion to complete the interfacial polymerization of the polyurethane polymer at the interface of the dispersed aqueous salt solution droplet. The average size of the microcapsule was controlled by the rate of mixing. Using the method of the invention, the following salt solutions were thereby prepared: (1) $Ca(NO_3)_2$ [5 molar]; (2) $K_2HPO_4$ [5 molar]; and (3) NaF [0.1 molar].

Example 2

A composition of the invention for cavity varnish with remineralization capabilities was prepared as follows. A standard cavity varnish containing rosin, ethanol and thymol (97 wt %) having the following remineralization agents (3 wt %) were combined with 1.5 wt % of a microcapsule containing a 1 M aqueous solution of potassium phosphate dibasic salt and 1.5 wt % of a microcapsule containing a 1 M solution of calcium nitrate.

Example 3

A composition for toothpaste with remineralization capabilities was prepared comprising a colloidal binding agent, humectants, preservatives, flavoring agents, abrasives, and detergents. 2 wt % of a microcapsule containing a 2 M aqueous solution of potassium phosphate dibasic and 2 wt % of a microcapsule containing a 1 M solution of calcium nitrate were incorporated. Additionally, microcapsules containing a 0.25 M solution of NaF were incorporated into the toothpaste as a therapeutic agent for fluoridation. Upon application to the oral cavity, the microcapsules will be burst in the mouth by the motion and pressure of a toothbrush against the teeth. The calcium ions will be released from the calcium nitrate solution to cause mineralization and whitening of the teeth.

Example 4

A composition for a dental resin composite with remineralization and therapeutic fluoridation capabilities was prepared as follows. A resin mixture (16 wt % total) was first made by combining urethane dimethacrylate resin with triethyleneglycoldimethacrylate (TEGDMA) resin in a 4/1 ratio. A photosensitizer (camphoroquinone) was added at 0.7 wt % of the total composition. An accelerator (ethyl-4-dimethylaminobenzoate) was added at 3 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, microcapsules containing a 2.5 M solution of calcium nitrate 1.25 wt %, microcapsules containing a 1.0 M solution of potassium phosphate dibasic 1.25 wt % and microcapsules containing a 0.25 M solution of NaF 0.5 wt %.

We claim:

1. A composition for topical administration, wherein the composition comprises a microcapsule composition comprising at least one polymer disposed as a semi-permeable shell around, and in direct contact with, an aqueous solution of at least one salt, the salt containing at least one salt ion, wherein the salt ion permeates through the shell, and wherein the composition is suitable for delivery to a mammal, and wherein (i) the aqueous solution is selected from the group consisting of a Ca(NO3)2 solution, a K2HPO4 solution, a NaF solution, and mixtures thereof, and (ii) the polymer is an amphiphilic polyurethane.

2. The composition of claim 1 wherein the molecular weight of the polymer is from about 1,000 g/mole to about 50,000 g/mole.

3. The composition of claim 1 wherein the microcapsule has a diameter of about 1 micron to about 3 mm.

4. A product for tissue mineralization comprising the composition of claim 1.

5. A bone mineralization product comprising the composition of claim 1 that causes an increase in bone mass of the mammal.

6. The bone mineralization product of claim 5 in the form of a bone cement or bioactive glass.

7. The composition of claim 1 wherein (i) the composition is a dental product for topical administration, and (ii) the salt ions prevent tooth demineralization or cause tooth remineralization within the oral cavity of the mammal.

8. The composition of claim 1 wherein the salt ions cause tooth whitening in the oral cavity of the mammal.

9. The composition of claim 1 wherein the salt ions cause a decrease in tissue sensitivity in the oral cavity of the mammal.

10. A dental product comprising the composition of claim 1 in the form of a paste, gel, foam, rinse, dentifrice, tooth whitening product, breath freshener, artificial saliva system, varnish, desensitizer, dental restorative, composite, adhesive, cement, bioactive glass, glass ionomer, compomer, giomer, resin, denture tooth, denture base material, root canal filler, sealer, dental implant tissue regeneration material, pulp capping material and filling restorative.

11. The composition of claim 10 further comprising an additive selected from the group comprising preservatives, antitartar, agents, anticalculus agents, antimicrobial agents, flavorings, sweeteners and dyes.

12. A tissue mineralization product comprising a plurality of the microcapsules of claim 1, wherein the microcapsules contain different aqueous salt solutions.

13. The composition of claim 1, wherein the composition comprises a plurality of microcapsules having different and distinct profiles of salt ion release, thereby permitting the controlled release of salt ions.

14. A product comprising as an active ingredient the composition of claim 1 selected from the group consisting of tablets, capsules, candies, lozenges and chewable gums.

15. A food material incorporating the composition of claim 1.

16. A method of loading the microcapsules of claim 1 with salt ions in the oral cavity, the method comprising contacting the microcapsules in the oral cavity with an aqueous salt solution wherein salt ions from the aqueous salt solution permeate through the semi-permeable polymer shell of the microcapsules into the microcapsules for subsequent use in tooth remineralization.

17. The method of claim 16 wherein the step of loading of the microcapsules results from administering into the oral cavity a dental product comprising said aqueous salt solution, wherein the dental product is selected from a paste, gel, foam, rinse, dentifrice, artificial saliva system, varnish, or adhesive.

18. A method of tooth remineralization comprising the steps of (1) administering into the oral cavity of a mammal a dental compound comprising the microcapsules of claim 1, and (2) releasing said salt ions out of the microcapsules into the oral cavity by mechanical agitation in the oral cavity.

19. The method of claim 18 wherein the salt ions are released from the microcapsules by a toothbrush, dental floss, teeth, or tongue.

20. An oral care product comprising the composition of claim 1.

21. The oral care product of claim 20, wherein the product is a dental product.

22. A dental product for reduction or prevention of caries comprising microcapsules, said microcapsules comprising amphiphilic polyurethane and containing an aqueous solution selected from at least one of $Ca(NO_3)_2$, $K_2HPO_4$ and NaF and wherein said microcapsules are prepared by an interfacial polymerization of a reverse emulsion.

23. A method of forming a microcapsule suitable for delivery to a mammal for use in tissue mineralization, the method comprising combining at least an amphiphilic polyurethane and at least one aqueous salt solution selected from the group consisting of a Ca(NO3)2 solution, a K2HPO4 solution, a NaF solution, and mixtures thereof, wherein the polymer forms a shell around the salt solution.

24. A method of forming microcapsules by surfactant free inverse emulsion interfacial polymerization suitable for delivery to mammals for tissue mineralization, the method comprising contacting (a) an aqueous salt solution selected from the group consisting of a Ca(NO3)2 solution, a K2HPO4 solution, a NaF solution, and mixtures thereof, (b) an oil phase, (c) an amphiphilic polyurethane polymer, and (d) an emulsifying agent, wherein the polymer forms a shell around the aqueous salt solution.

25. The method of claim 23 or 24 wherein the shell is semi-permeable or non-permeable.

26. The method of claim 23 or 24 wherein the tissue is bone or tooth.

27. The method of claim 23 or 24 wherein the mammal is a human.

28. The method of claim 24 further comprising adding a diol, an isocyanate or both.

29. The method of claim 24 wherein the oil phase is methyl benzoate.

30. The method of claim 24 wherein the emulsifying agent is a polyglyceryl-3-polyricinoleate.

31. A method of forming semi-permeable polymer microcapsules by surfactant free inverse emulsion interfacial polymerization suitable for delivery to mammals for tissue mineralization, the method comprising contacting (a) an aqueous solution, (b) an oil phase, (c) an amphiphilic polyurethane polymer, and (d) an emulsifying agent, wherein the polymer forms a semi-permeable shell layer around the aqueous solution, the solution, selected from the group consisting of a Ca(NO3)2 solution, a K2HPO4 solution, a NaF solution, and mixtures thereof, and wherein the tissue is bone or tooth.

32. A method of increasing bone mass or preventing loss of bone mass in bone of a mammal, the method comprising locally administering to said bone a compound comprising microcapsules containing an aqueous solution of salt encapsulated by a semi-permeable amphiphilic polyurethane polymer shell, the aqueous solution is selected from the group consisting of a Ca(NO3)2 solution, a K2HPO4 solution, a NaF solution, and mixtures thereof, said aqueous salt solution releasing salt ions that permeate out of the microcapsules through the semi-permeable shell, in an amount sufficient to induce mineralization of the bone and thereby to increase bone mass or to prevent loss of bone mass.

33. A method of tooth remineralization comprising administering into the oral cavity of a mammal a dental compound comprising microcapsules containing an aqueous solution of salt encapsulated by a semi-permeable amphiphilic polyurethane polymer shell, the aqueous solution is selected from the group consisting of a Ca(NO3)2 solution, a K2HPO4 solution, a NaF solution, and mixtures thereof, said aqueous salt solution releasing salt ions that permeate out of the microcapsules through the semi-permeable shell into the oral cavity.

34. The method of claim 33 wherein the salt ions also cause whitening of the teeth in the oral cavity.

35. The method of claim 33 wherein said dental compound is selected from a paste, gel, foam, rinse, dentifrice, whitening product, breath freshener, artificial saliva system, varnish, desensitizer, dental restorative, composite, adhesive, cement, bioactive glass, glass ionomer, compomer, resin, denture tooth, denture base material, root canal filler, sealer, dental implant tissue regeneration material, pulp capping material and filling restorative.

* * * * *